United States Patent [19]

Gupta et al.

[11] Patent Number: 5,074,247

[45] Date of Patent: Dec. 24, 1991

[54] INSECT CONTAINING TEST APPARATUS

[75] Inventors: Raj K. Gupta, Walkersville, Md.; Louis C. Rutledge, Mill Valley, Calif.; William J. Letourneau, Grafton, Mass.

[73] Assignee: The United States of America as represented by the Secretary of the Army, Washington, D.C.

[21] Appl. No.: 652,857

[22] Filed: Feb. 11, 1991

[51] Int. Cl.$^5$ ............................................. A01K 29/00
[52] U.S. Cl. ...................................... 119/6.5; 119/15
[58] Field of Search .......................... 119/6.5, 15, 17

[56] References Cited

U.S. PATENT DOCUMENTS

| | | | |
|---|---|---|---|
| 2,174,305 | 9/1939 | Austin | 119/6.5 |
| 3,397,676 | 8/1968 | Barney | 119/15 |
| 3,413,958 | 12/1968 | Artig | 119/15 |
| 3,580,219 | 5/1971 | Stebbins | 119/6.5 |
| 3,626,902 | 12/1971 | Orfei | 119/17 |
| 3,874,335 | 4/1975 | Galasso | 119/6.5 |
| 4,212,267 | 7/1980 | Patterson | 119/6.5 |
| 4,252,080 | 2/1981 | Gioia et al. | 119/6.5 |

Primary Examiner—John G. Weiss
Attorney, Agent, or Firm—Werten F. W. Bellamy; Anthony T. Lane

[57] ABSTRACT

An insect containing test apparatus which is applied to a skin region of a test subject includes a rectangular slide and test cage made of a clear, autoclavable polycarbonate plastic. The test cage is injection molded to a generally rectangular shape and includes a peripheral flange extending outwardly from sides at an open top. A screen member covering the open top is then heat pressed onto this flange. Test holes are also punched into the bottom the test cage. During injection molding, U-shaped channels along each respective longitudinal side adjacent the bottom are also provided to receive the slide so that the slide is selectively moved to cover and uncover the test holes in the bottom.

6 Claims, 1 Drawing Sheet

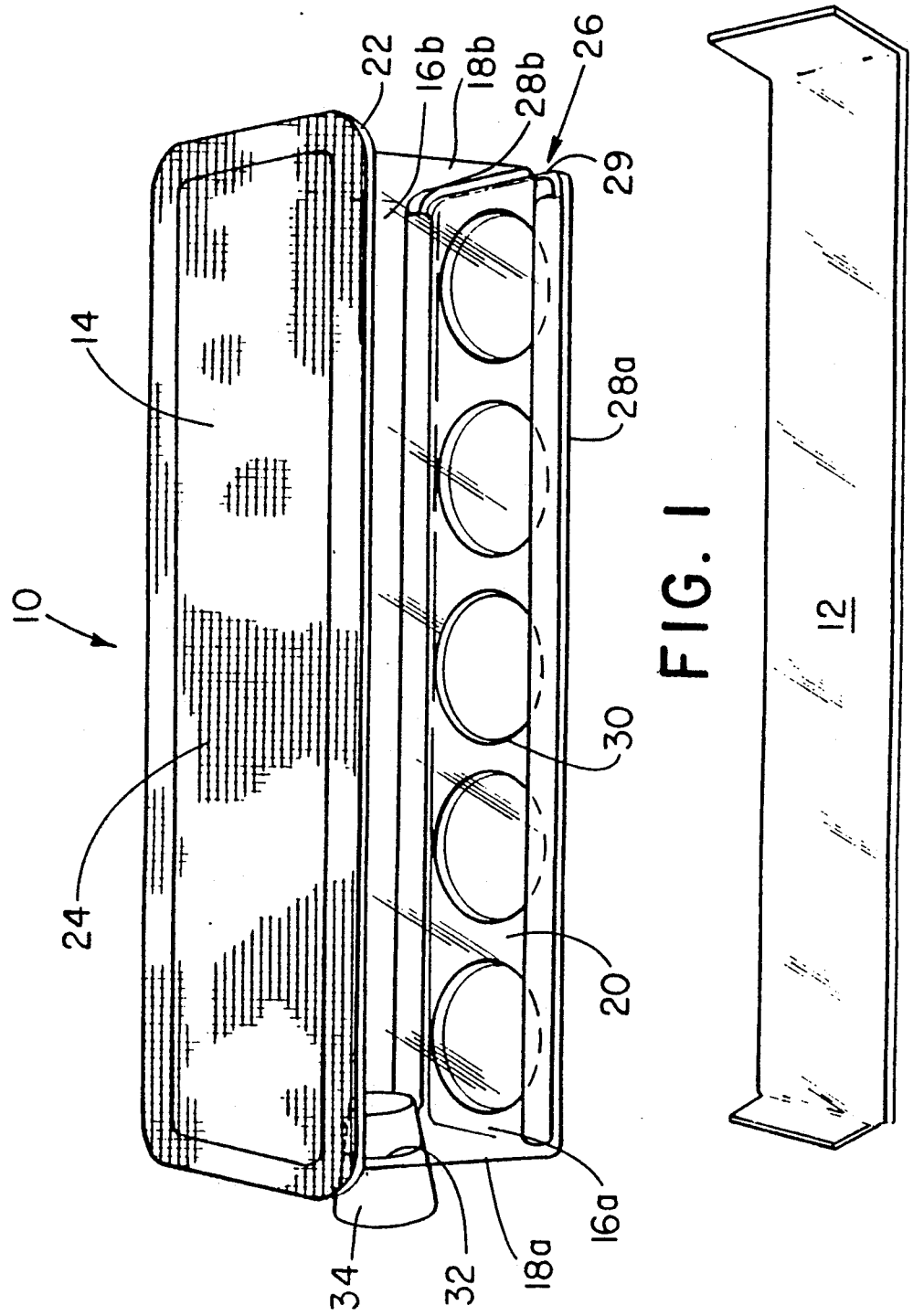

INSECT CONTAINING TEST APPARATUS

FIELD OF THE INVENTION

The present invention relates generally to an insect containing test apparatus for testing repellents on human volunteers, and more particularly to an improved test apparatus, which is inexpensive, easy to make, and autoclavable.

BACKGROUND OF THE INVENTION

The recent introduction of sustained-released technology and topical repellent formulations has resulted in a surge of activity to evaluate these formulations against biting arthropods. Many such evaluations are conducted using a test apparatus such as described in the American Society for Testing Materials (ASTM) Designation Standard E951-89 "Standard Test Methods for Laboratory Testing of Non-Commercial Mosquito Repellent Formulations On the Skin". The test apparatus described in the Standard is made of PLEXIGLASS and includes a cellulose acetate slide. This test apparatus is handcrafted, which makes it expensive ($25 to $34 per apparatus) and nonexpendable. In addition, this apparatus cannot be autoclaved so that cleaning and drying problems preclude immediate reuse.

Various other cages or the like have been disclosed in the prior art. For example, in U.S. Pat. No. 3,413,958 (Artig), a pet animal shelter having a clear plastic top is disclosed. An educational observatory for insects including a transparent plastic top is also disclosed in U.S. Pat. No. 3,626,902 (Orfei). Another insect study station having an elongated, transparent cylinder which might be made of glass, acrylic, or polyvinyl chloride is disclosed in U.S. Pat. No. 4,212,267 (Patterson).

SUMMARY OF THE INVENTION

In accordance with the present invention, an insect containing test apparatus which is applied to a skin region of a test subject includes a rectangular slide and a generally rectangular parallelpiped cage both made of a clear, autoclavable polycarbonate plastic. The cage has an open top, longitudinal sides, lateral sides, a bottom in which test holes are provided, and a receiving means for slidably receiving the slide in the cage adjacent the test holes. Thus, it will be appreciated that the test holes are selectively covered and uncovered by movement of the slide. A hole is also provided in one lateral side for the introduction of insects into the cage, and a stopper is provided which normally fills this hole. A screen member covers the open top of the cage.

In the preferred embodiment, the cage is injection molded and includes a peripheral flange extending outwardly from the sides at the top to which the screen member is attached. In addition, the receiving means includes a U-shaped channel injection molded in each respective longitudinal side adjacent to the bottom.

A preferred method of making the insect containing test apparatus includes the making of the slide and the injection molding of the cage. Test holes are provided in the bottom of the cage by punching, and the screen member is attached to the top of the cage by heat-pressing. In the preferred embodiment, a peripheral flange is provided by the injection molding step to which the screen member is heat pressed. In addition, the injection molding step also includes the step of forming a U-shaped channel along each respective longitudinal side of the test cage so that the slide is slidably received in these channels.

It is an advantage of the present the invention that an inexpensive test apparatus is provided, which can be expendable due to its low cost.

It is also an advantage of the present invention that a test apparatus is provided which is autoclavable and thus able to be reused immediately.

It is a further advantage of the present invention that a test apparatus is provided which is easily made.

Other features and advantages of the present invention are stated and are apparent from a detailed description of a presently preferred embodiment of the invention found hereinbelow.

BRIEF DESCRIPTION OF THE DRAWINGS

FIG. 1 is a schematic perspective view of a test cage according to the present invention.

FIG. 2 is a perspective view of a slide which is received in the test cage depicted in FIG. 1.

DETAILED DESCRIPTION OF THE PREFERRED EMBODIMENT

With reference now to the drawings in which like numerals represent like elements, an insect containing test apparatus is depicted in FIGS. 1 and 2 and comprises a test cage 10 and a slide 12 which is received in test cage 10. It will be appreciated by those of ordinary skill in the art that the test apparatus of the present invention is an improvement to be substituted for the similar test apparatus of the prior art described in ASTM Standard E951-89, which Standard is hereby incorporated by reference. Thus, it will also be appreciated that the test apparatus of the present invention has the same approximate dimensions (18 by 5 by 4 cm) and other such standard features disclosed in the Standard so as to be usable as a substitute therefor.

As shown in FIG. 1, test cage 10 is in the form of a generally rectangular parallelpiped cage and includes an open top 14, longitudinal sides 16a and 16b, lateral sides 18a and 18b, and a bottom 20. It should be appreciated that test cage 10 and slide 12 are made of a suitable clear polycarbonate plastic, such as LEXAN. Thus, test cage 10 and slide 12 offer unique properties including clarity, stability, toughness, autoclavability, and non-toxicity to test organisms.

Test cage 10 is preferably injection molded in an easy and simple procedure. During this injection molding, a peripheral flange 22 is provided extending outwardly from sides 16a, 16b, 18a, and 18b at open top 14. Subsequently, a screen member 24 is heat-pressed onto peripheral flange 22 to close open top 14. During the injection molding, it should also be appreciated that a receiving means 26 for slidably receiving slide 12 adjacent bottom 20 is provided. Preferably, receiving means 26 takes the form of U-shaped channels 28a and 28b provided in respective longitudinal sides 16a and 16b adjacent bottom 20. Receiving means 26 also includes an opening 29 in lateral side 18b through which slide 12 is received into channels 28a and 28b.

After the injection forming of test cage 10, a series of test holes 30 are punched in bottom 20. These test holes are preferably in conformance with the standard discussed above, in relation both to size and spacing as well as the number of test holes. In addition, a hole 32 is provided in lateral side 18a for the introduction of insects into test cage 10. Normally, a stopper 34 fills this hole.

In use, the test apparatus of the present invention is used in the same manner as described in the referenced ASTM Standard. In particular, five circular test areas are outlined on the flexor region of the forearm of the test subject, which regions are then treated with the diluent and four serial dilutions of a test repellent. Test cage 10 having matching test holes 30 and provided with slide 12 as well as a number of mosquitos or other insects is then attached to the forearm of the user. Subsequently, slide 12 is slid backward to uncover all test holes 30. The numbers of mosquitos feeding on the control and repellent treatment areas are then viewed through test cage 10 and recorded as test cage 10 provides condensate-free visibility for the observation of biting mosquitos. After the trial period is over, slide 12 is reinserted into test cage 10 to cover test holes 30. It should be appreciated that slide 12 slides freely in test cage 10 while being received in both U-shaped channels 28a and 28b.

A series of experiments were conducted to determine if there was any significant difference in efficacy data between the test apparatus of the present invention and that disclosed in the ASTM Standard. Test results indicated no significant difference between the test apparatus of the present invention and the ASTM Standard test cages. Thus, it will be appreciated that evaluations using the test apparatus of the present invention can be compared with that using the ASTM Standard cages.

While the present invention has been described with respect to an exemplary embodiment thereof, it will understood by those of ordinary skill in the art that variations and modifications can be effected within the scope and spirit of the invention.

We claim:

1. An insect containing test apparatus which is applied to a skin region of a test subject comprising:
    a rectangular slide made of a clear, autoclavable polycarbonate plastic;
    a generally rectangular parallelpiped cage made of a clear, autoclavable polycarbonate plastic, said cage having an open top, longitudinal sides, lateral sides, a bottom in which test holes are provided, and a receiving means for slidably receiving said slide in said cage adjacent said test holes whereby said test holes are selectively covered and uncovered by movement of said slide;
    a hole in one said lateral sides for the introduction of insects into said cage and a stopper which normally fills said hole; and
    a screen member covering said open top of said cage.

2. A test apparatus as claimed in claim 1 wherein said cage is injection molded and includes a peripheral flange extending outwardly from said sides at said open top to which said peripheral flange said screen member is attached.

3. A test apparatus as claimed in claim 2 wherein said receiving means includes a U-shaped channel injection molded in each respective said longitudinal side adjacent said bottom.

4. A method of making an insect containing test apparatus which is applied to a skin region of a user comprising the steps of:
    making a rectangular slide of a clear, autoclavable polycarbonate plastic;
    injection molding a clear autoclavable polycarbonate plastic to form a generally rectangular parallelpiped cage, the cage including an open top, longitudinal sides, lateral sides, a bottom and a receiving means for slidably receiving the slide in the cage adjacent the bottom;
    punching a plurality of test holes in the bottom of the cage such that the test holes are selectively covered and uncovered by movement of the slide; and
    heat-pressing a screen member on the top of the cage.

5. A method of making a test apparatus as claimed in claim 4 wherein said injection molding step includes the step of forming a peripheral flange extending outwardly from the sides at the open top, and wherein said heat-pressing step includes the heat pressing of the screen member to the peripheral flange.

6. A method of making a test apparatus as claimed in claim 5 wherein said injection molding step further includes the step of forming an opening in one lateral side adjacent the bottom and a U-shaped channel beginning at said opening and extending along each respective longitudinal side adjacent the bottom such that the slide is slidably received in the channels.

* * * * *